United States Patent [19]

George et al.

[11] Patent Number: 4,818,054

[45] Date of Patent: Apr. 4, 1989

[54] DISTRIBUTION FRAME FOR OPTICAL FIBERS

[75] Inventors: Edward K. George, South Hornchurch; Roger E. Jung, London; Brian P. Mills, Hornchurch, all of England

[73] Assignee: Telephone Cables Limited, England

[21] Appl. No.: 126,754

[22] Filed: Nov. 30, 1987

[30] Foreign Application Priority Data

Dec. 12, 1986 [GB] United Kingdom ................ 8629707

[51] Int. Cl.$^4$ ............................................... G02B 6/36
[52] U.S. Cl. ............................. 350/96.20; 350/96.21; 350/96.22
[58] Field of Search ............... 350/96.20, 96.21, 96.22, 350/96.15, 96.10

[56] References Cited

FOREIGN PATENT DOCUMENTS

| | | | |
|---|---|---|---|
| 0149250 | 7/1985 | European Pat. Off. | 350/96.20 |
| 3118173 | 11/1982 | Fed. Rep. of Germany | 350/96.20 |
| 74517 | 4/1984 | Japan | 350/96.20 |
| 128208 | 6/1984 | Japan | 350/96.20 |
| 162208 | 8/1985 | Japan | 350/96.20 |
| 85/04960 | 11/1985 | PCT Int'l Appl. | 350/96.20 |
| 2166262 | 4/1986 | United Kingdom | 350/96.20 |

Primary Examiner—William L. Sikes
Assistant Examiner—Frank González
Attorney, Agent, or Firm—Kirschstein, Kirschstein, Ottinger & Israel

[57] ABSTRACT

A distribution frame for an optical fibre transmission system comprises a cabinet incorporating at each side at least one side panel supporting a surplus length of cable, a pair of inner panels spaced from the side panels and organizer trays, arranged to accommodate surplus lengths of fibres from the cables, supported between the inner panels, the latter panels also supporting couplers for enabling the cable fibers to be connected to further fibres, the ends of which are accommodated in the spaces between the inner and side panels.

11 Claims, 3 Drawing Sheets

DISTRIBUTION FRAME FOR OPTICAL FIBERS

BACKGROUND OF THE INVENTION

This invention relates to distribution frames for optical fibre transmission systems, such distribution frames being arranged to accommodate connections between optical fibre cables and individual optical fibres, hereinafter referred to as connection fibres.

The distribution frames may be required to provide connections between a plurality of optical cables and a respective multiplicity of connection fibres which may be in the form of single or multifibre elements or cords, having the fibre or fibres protected by an outer coating or cover, and an object of the invention is to provide a particular advantageous form of distribution frame which is suitable for such a purpose.

SUMMARY OF THE INVENTION

According to the invention a distribution frame for an optical fibre transmission system comprises a cabinet incorporating at each side at least one panel having means for supporting a surplus length of cable, a pair of relatively spaced inner panels spaced from the adjacent side panels and substantially parallel thereto, and a plurality of organiser trays supported between the inner panels and arranged to accommodate surplus lengths of fibres from the cables, the spaces between the inner and side panels being arranged to accommodate the end parts of a multiplicity of connection fibres, and the inner panels being provided with a multiplicity of openings designed to support couplers for enabling connections to be made between fibres from the organiser trays and those of respective connection fibres. The cabinet used may be from 2.2 m to 2.6 m in height with base dimensions of 900 mm × 520 mm. Such cabinets have a capacity of up to 960 terminated connectors.

Conveniently the distribution frame incorporates a plurality of side panels at each side of the frame, each arranged to accommodate a respective length of cable in the form of a loop. For this purpose the edges of each panel are bent over to provide inwardly facing channels into which the loop of cable may be fitted.

The organiser trays are preferably in the form of relatively slidable drawers, the drawers conveniently being disposed in groups each arranged to accommodate the fibres of a respective cable. Where the optical cables comprise a series of stranded tubes each accommodating a plurality of fibres, the fibres of different tubes are conveniently accommodated in different organiser trays of a respective group.

Conveniently, a plurality of cables and connection fibres exit from the frame at the top and/or the bottom of the space between the respective inner and side panels, the parts of the connection fibres within the spaces preferably hanging in loose loops.

The connection fibres conveniently exit from the respective spaces between pairs of resilient separating straps, the straps also serving to bear against the sides of the connection fibres and retain them in position. Such an arrangement enables the connection fibres to be readily introduced into the frame and, at the same time provides a simple yet effective way of supporting them without risk of damage.

A distribution frame in accordance with the invention has the advantage that it can be constructed in a relatively compact manner whilst accommodating a plurality of multifibre cables, with respective connection fibres, the surplus lengths of cable and fibres facilitating the reconnection of fibres to the connectors in the event of fibre breakage. Thus a distribution frame in accordance with the invention can readily be constructed to terminate six 160-fibre cables in a relatively small volume, whilst still providing ready access to the fibre ends and respective conductors; in such an arrangement the cables are conveniently arranged to enter the frame in two groups of three, with the surplus lengths of the two groups of cable accommodated in respective side panels at opposite sides of the frame. Moreover sharp bends in the cables and fibres which would give rise to excessive attenuation are readily avoided.

BRIEF DESCRIPTION OF THE DRAWINGS

One distribution frame in accordance with the invention will now be described by way of example with reference to FIGS. 1 to 4 of the accompanying schematic drawings, in which.

DETAILED DESCRIPTION OF THE PREFERRED EMBODIMENT

The distribution frame is in the form of a cabinet having a structural framework consisting of a rectangular base 1 with a support post 2 extending upwards from each corner, the support posts being held rigidly in position by cross-bracings 3 (only some of which are shown) at the top and in intermediate positions. The structural frame work can be of modular form so as to be capable of being separated into sections for ease of installation.

Figure 1:
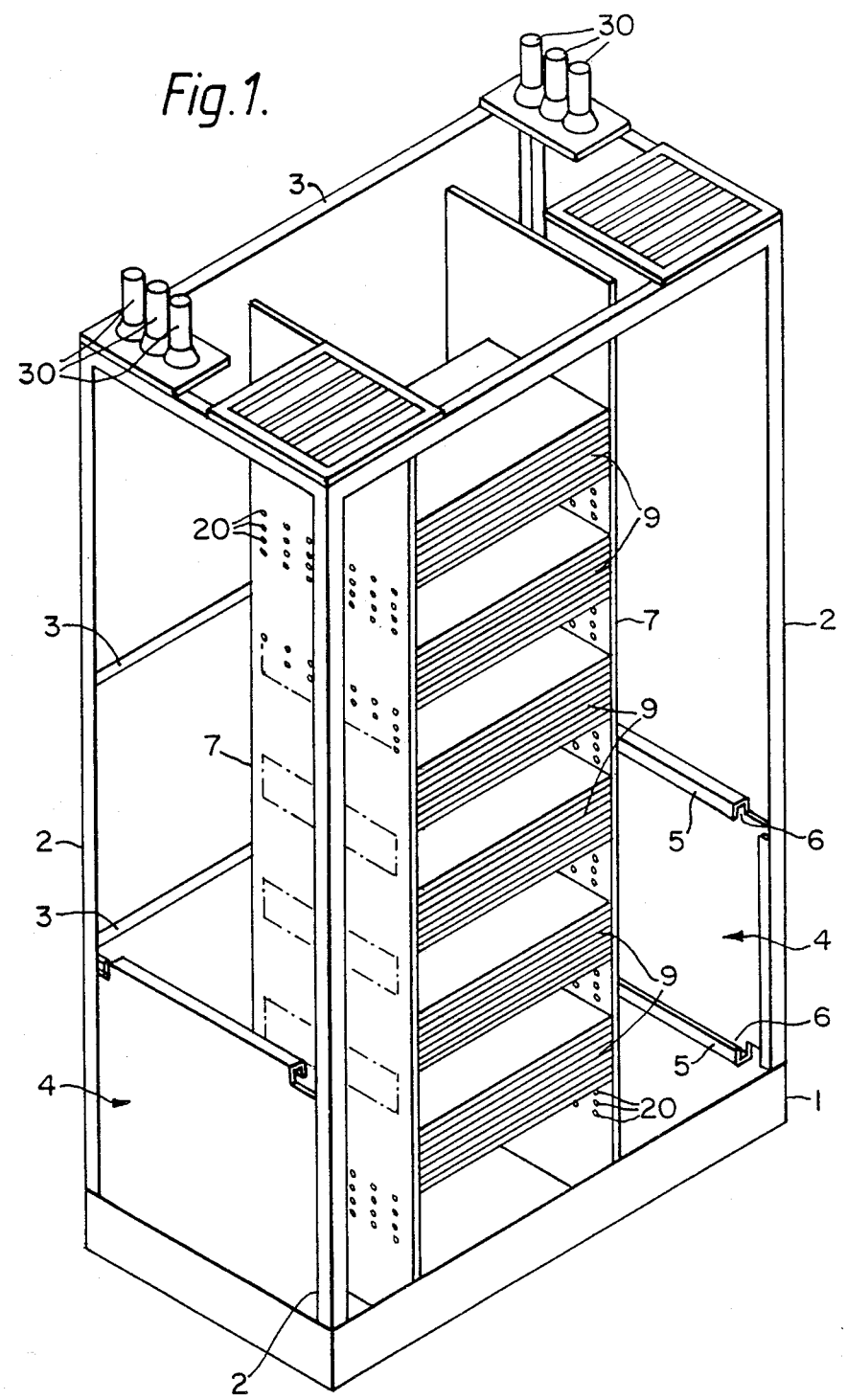
FIG. 1 represents a perspective view of the partly assembled frame in diagrammatic form.
Figure 3:
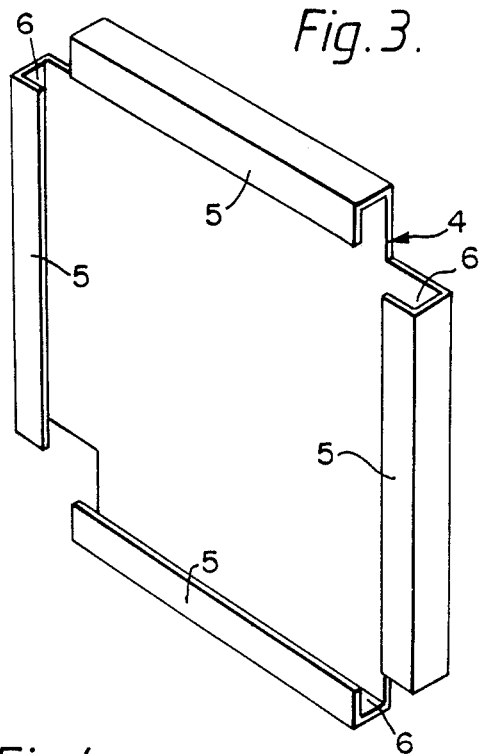
FIG. 3 represents a perspective view of one of the side panels employed in the frame.
Figure 4:
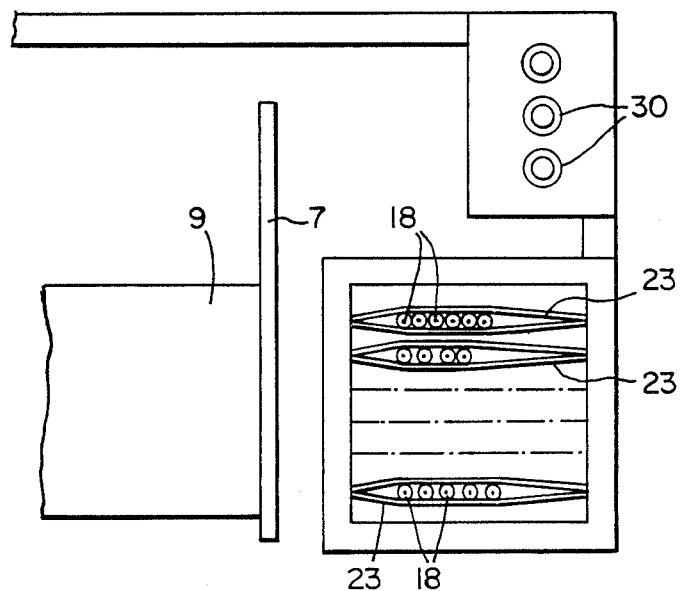
FIG. 4 represents a perspective view of the part of the top of the frame.

To the two support posts 2 at each side of the framework there are attached three superposed sheet metal panels 4, two only of which are shown in FIG. 1. Each of these panels is in the form of a tray, as shown more clearly in FIG. 3, with the edges 5 turned over to provide inwardly facing channels 6, the panels 4 being fixed to the support posts 2 with the inturned edges facing the interior of the frame.

Figure 2:
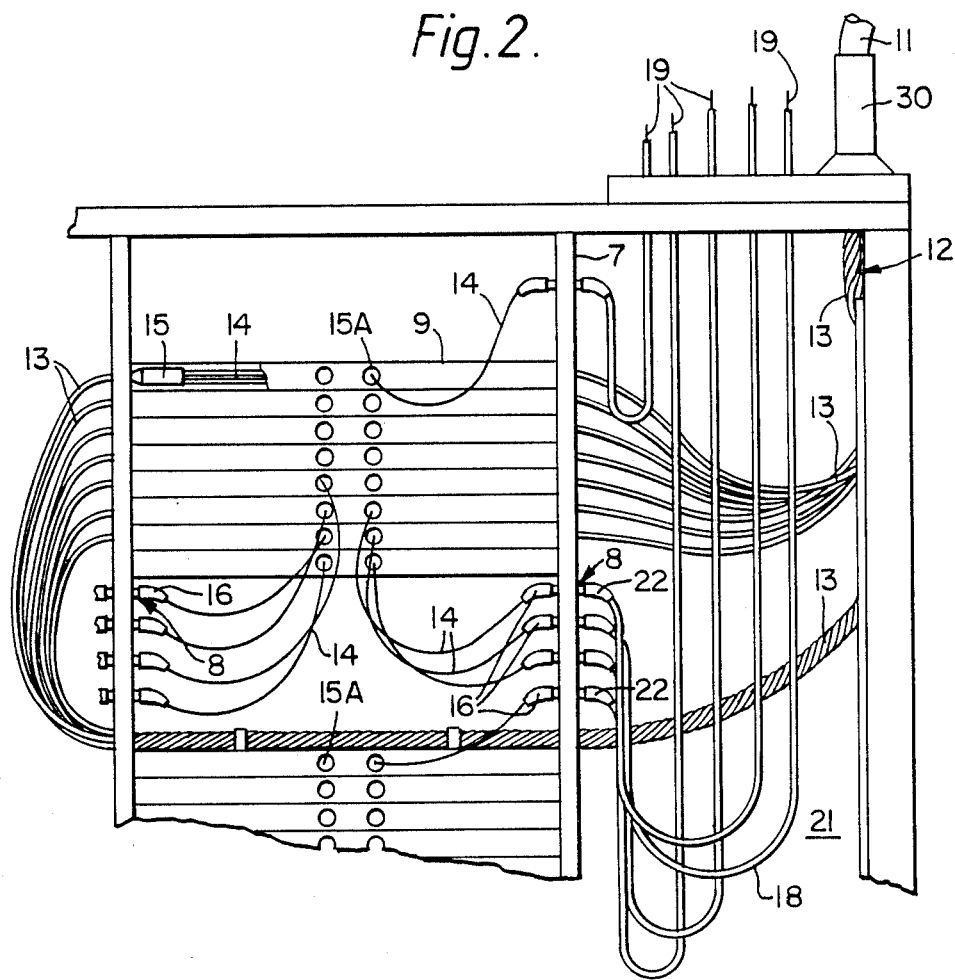
FIG. 2 represents an enlarged view of part of the rear of the frame.

Two inner panels 7, extending the full height of the frame, are disposed between the outer panels 4 and parallel to them, the inner panels being spaced from each other and from the outer panels. These inner panels are formed with a multiplicity of perforations 20 regularly arranged in rows and columns, and providing supports for optical fibre bulkhead couplers 8 (see FIG. 2).

Six groups of organiser trays 9 are supported between the inner panels 7, each group consisting of eight trays in the form of relatively slidable drawers.

The distribution frame is arranged to provide terminations for six 160-fibre cables 11 entering into the spaces 21 between the inner and side panels 4, 7 through cable entry sleeves 30 of known kind disposed in two groups of three at the top of the frame. Approximately three metres of a prepared length 12 of cable, that is to say cable having its outer sheath removed to expose sixteen fibre unit tubes 13, loosely accommodating one hundred and sixty optical fibres, is stored in a respective one of the panels 4, by being lodged in loop form within the channels 6 formed by the inturned edges 5 of the panel 4.

The unit tubes 13 from each cable radiate from the associated storage panel 4 to respective one of the groups of organiser trays 9, the individual fibres 14 extending into an appropriate organiser tray through a protective manifold 15. Each organiser tray 9 is arranged to store approximately 1.5 meters lengths of twenty fibres looped around the tray with a curvature sufficiently large so as not to cause local attenuation, the fibres 14 being disposed in two groups of ten and exiting through a port 15A at the back of the tray. Each fibre 14 terminates in one element 16 of a respective bulkhead coupler 8 which can be fitted directly on to the main cable fibre without splicing, or on prepared tails spliced to the main cable fibre within the organiser tray. The outgoing optical fibres which are conveniently in the form of cords 18, that is to say with each individual fibre protected by an outer coating or cover, are located within the space 21 between the respective inner panel 7 and the adjacent side panels 4, the fibres 19 of the units being connected to co-operating elements 22 of the bulkhead couplers 8.

The cords 18 pass from the spaces 21 between pairs of resilient separating straps 23 which engage the sides of the cords and also serve to support them, the parts of the cords within the spaces being loosely looped as shown.

The inner panels conveniently carry suitable markings to enable the location of individual connectors to be readily identified.

Removable panels (not shown) close the front of the frame in use.

The invention enables the distribution frame to be constructed with a width comparable with those of the cabinets of existing telephone exchange equipment, the frame conveniently being fitted with cladding and corner pieces so that it has the same appearance as adjacent equipment.

However excessive bends which could cause attenuation in the optical fibres 14 and 19 is avoided, and ready access may be gained both to the cable fibres 14, and to the unit fibres 19, as well as to the connectors 8.

Copper pairs (not shown) in the optical fibre cables are conveniently terminated on modules fitted with I.D.C. contacts, a gland being provided to secure the internal copper conductors to the frame.

The use of the resilient separating straps 23 enable the optical fibre cords to be readily introduced into the frame and support the units without risk of damage to the optical fibres within them. Accordingly such straps may be used to advantage for supporting optical fibre cords in other forms of distribution frames.

We claim:

1. A distribution frame for an optical fibre transmission system, comprising:
    (a) a cabinet having side panels bounding an interior in which surplus lengths of optical fibre cables in loop form are accommodated,
    (b) a pair of relatively spaced inner panels spaced from the side panels and substantially parallel thereto, and
    (c) a plurality of organiser trays supported by and occupying the space between the inner panels and each tray being arranged to accommodate surplus lengths of several fibres from the cables,
    (d) the inner and side panels being spaced apart to accommodate the end parts of a multiplicity of connection fibres for connection to respective fibres from the organiser trays, and
    (e) the inner panels being provided with a multiplicity of openings to support couplers for enabling connections to be made through those openings between fibres from the organiser trays and the respective connection fibres.

2. A distribution frame according to claim 1 incorporating a plurality of side panels at each side of the frame, each arranged to support a respective length of cable in loop form parallel to a respective side panel.

3. A distribution frame according to claim 2 wherein the side edges of each side panel are bent over to provide inwardly facing channels for accommodating the loop cable.

4. A distribution frame according to claim 1, wherein the organiser trays are in the form of relatively slidable drawers.

5. A distribution frame according to claim 4 wherein the drawers are disposed in groups each arranged to accommodate the fibres of a respective cable.

6. A distribution frame according to claim 1, wherein a plurality of cables and individual connection fibres exit from the top of the space between the respective inner and side panels.

7. A distribution frame according to claim 1 wherein a plurality of cables and individual connection fibres exit from the bottom of the space between the respective inner and side panels.

8. A distribution frame according to claim 6 wherein a plurality of cables and individual connection fibres exit from the bottom of the space between the respective inner and side panels.

9. A distribution frame according to claim 6 comprising pairs of resilient separating straps mounted within said space for supporting the connection fibres as they exit said space.

10. A distribution frame according the claim 9 wherein the connection fibres are in the form of cords.

11. A distribution frame according to claim 1, wherein each side panel has thereon means for supporting the surplus lengths of the optical fibre cables.

* * * * *